United States Patent
Brown

(10) Patent No.: US 10,433,760 B2
(45) Date of Patent: Oct. 8, 2019

(54) CONTROL OF BREATHING DURING MRI-BASED PROCEDURES

(71) Applicant: ELEKTA AB (PUBL), Stockholm (SE)

(72) Inventor: Kevin Brown, Horsham (GB)

(73) Assignee: ELEKTA AB (PUBL), Stockholm (SE)

( * ) Notice: Subject to any disclaimer, the term of this patent is extended or adjusted under 35 U.S.C. 154(b) by 308 days.

(21) Appl. No.: 15/320,116

(22) PCT Filed: Jun. 10, 2015

(86) PCT No.: PCT/EP2015/062942
§ 371 (c)(1),
(2) Date: Dec. 19, 2016

(87) PCT Pub. No.: WO2015/197363
PCT Pub. Date: Dec. 30, 2015

(65) Prior Publication Data
US 2017/0135599 A1    May 18, 2017

(30) Foreign Application Priority Data

Jun. 25, 2014 (GB) .................................. 1411246.0

(51) Int. Cl.
*A61B 5/055* (2006.01)
*A61B 5/00* (2006.01)
(Continued)

(52) U.S. Cl.
CPC .............. *A61B 5/055* (2013.01); *A61B 5/113* (2013.01); *A61B 5/7292* (2013.01);
(Continued)

(58) Field of Classification Search
None
See application file for complete search history.

(56) References Cited

U.S. PATENT DOCUMENTS

| 5,363,844 A | 11/1994 | Riederer et al. |
| 7,393,329 B1 | 7/2008 | Wong et al. |
| 2011/0201919 A1 | 8/2011 | Allen et al. |

FOREIGN PATENT DOCUMENTS

| EP | 1369085 A1 | 12/2003 |
| EP | 2423699 A1 | 2/2012 |

(Continued)

OTHER PUBLICATIONS

Liu Y L et al: "A Monitoring, Feedback, and Triggering System for Reproducible Breath-Hold MR Imaging," Magnetic Resonance in Medicine, vol. 30, No. 4, Oct. 1, 1993, pp. 507-511.

(Continued)

*Primary Examiner* — Brian T Gedeon
(74) *Attorney, Agent, or Firm* — Finnegan, Henderson, Farabow, Garrett & Dunner LLP

(57) ABSTRACT

The valve of an active breathing control (ABC) device can be driven by the output of the navigator channel of the MRI scanner, rather than by inference from a measured breath flow rate. Where the MRI scanner is integrated with a radiotherapy device, the MRI data can be used to trigger the enforced breath-hold by the ABC, and the radiotherapy delivered while the ABC valve is shut. If the MRI data pertains to the actual position of the tumor, then the ABC device will (in effect) hold the tumor at a precise and reproducible point for treatment.

20 Claims, 2 Drawing Sheets

(51) Int. Cl.

| | |
|---|---|
| *G01R 33/48* | (2006.01) |
| *A61M 16/20* | (2006.01) |
| *G01R 33/567* | (2006.01) |
| *G01R 33/565* | (2006.01) |
| *A61N 5/10* | (2006.01) |
| *A61M 16/06* | (2006.01) |
| *A61B 5/113* | (2006.01) |
| *G01R 33/28* | (2006.01) |
| *A61M 16/00* | (2006.01) |

(52) U.S. Cl.
CPC .......... *A61M 16/021* (2017.08); *A61M 16/06* (2013.01); *A61M 16/202* (2014.02); *A61N 5/1068* (2013.01); *G01R 33/28* (2013.01); *G01R 33/4812* (2013.01); *G01R 33/5676* (2013.01); *G01R 33/56509* (2013.01); *A61B 5/4887* (2013.01); *A61M 2205/33* (2013.01); *A61N 2005/1055* (2013.01)

(56) References Cited

FOREIGN PATENT DOCUMENTS

| JP | H0826650 A | 1/1996 |
|---|---|---|
| JP | H08266500 A | 10/1996 |
| JP | H08266501 A | 10/1996 |
| WO | WO-2009/007737 A1 | 1/2009 |
| WO | WO-2010/150209 A1 | 12/2010 |

OTHER PUBLICATIONS

Johannes F.T. Arnold et al: "Lung MRI Using an MR-Compatible Active Breathing Control (MR-ABC)," Magnetic Resonance in Medicine, vol. 58, No. 6, Nov. 28, 2007, pp. 1092-1098.

Krauss D J et al: "MRI-Based Volumetric Assessment of Cardiac Anatomy and Dose Reduction Via Active Breathing Control During Irradiation for Left-Sided Breast Cancer," International Journal of Radiation: Oncology Biology Physics, vol. 61, No. 4, Mar. 15, 2005, pp. 1243-1250.

Wright R C et al: "Real-Time MR Fluoroscopic Data Acquisition and Image Reconstruction," Magnetic Resonance in Medicine, vol. 12, No. 3, Dec. 1, 1989, pp. 407-415.

Kaza E et al: "First MRI Application of an Active Breathing Coordinator," Physics in Medicine and Biology, Institute of Physics, vol. 60, No. 4, Jan. 29, 2015, pp. 1681-1696.

MedicalPhysicsWeb: "Breath-Hold MRI Enhances Treatment Plans," Mar. 3, 2015, Retrieved from the Internet: URL:http://medicalphysicsweb.org/cws/article/research/60401, the whole document.

UK Intellectual Property Office Search Report in GB1411246.0, dated Jan. 13, 2015, 2 pages.

International Search Report in PCT/EP2015/062942, dated Sep. 9, 2015. 17 pp.

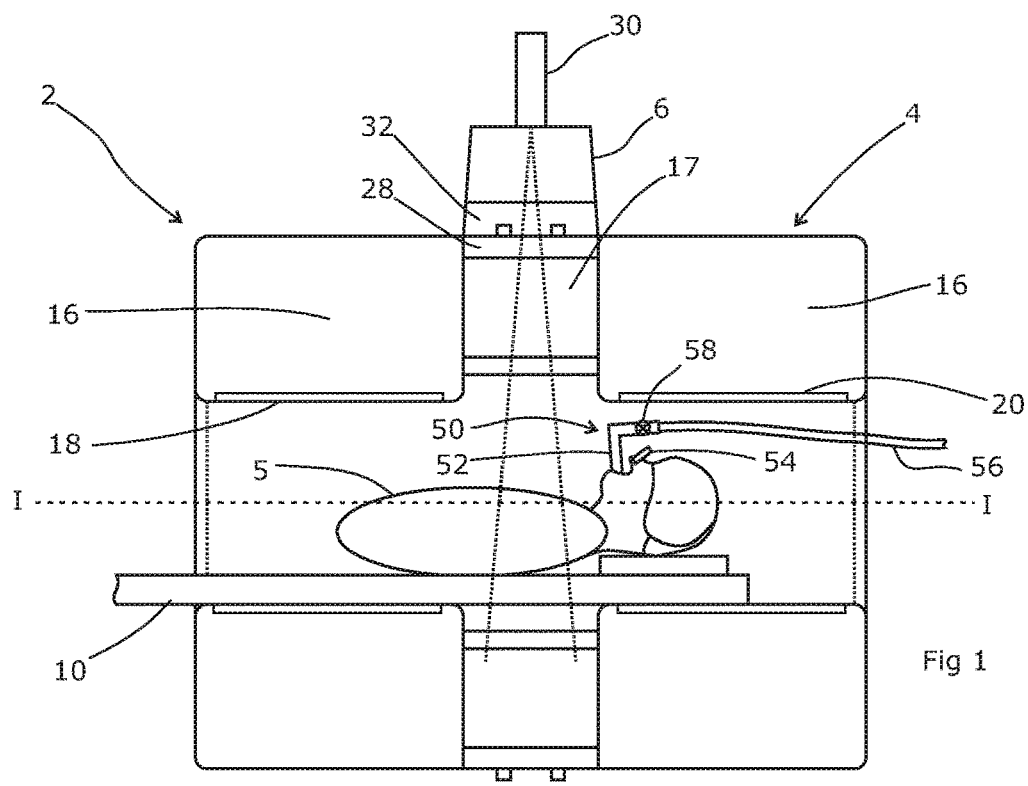
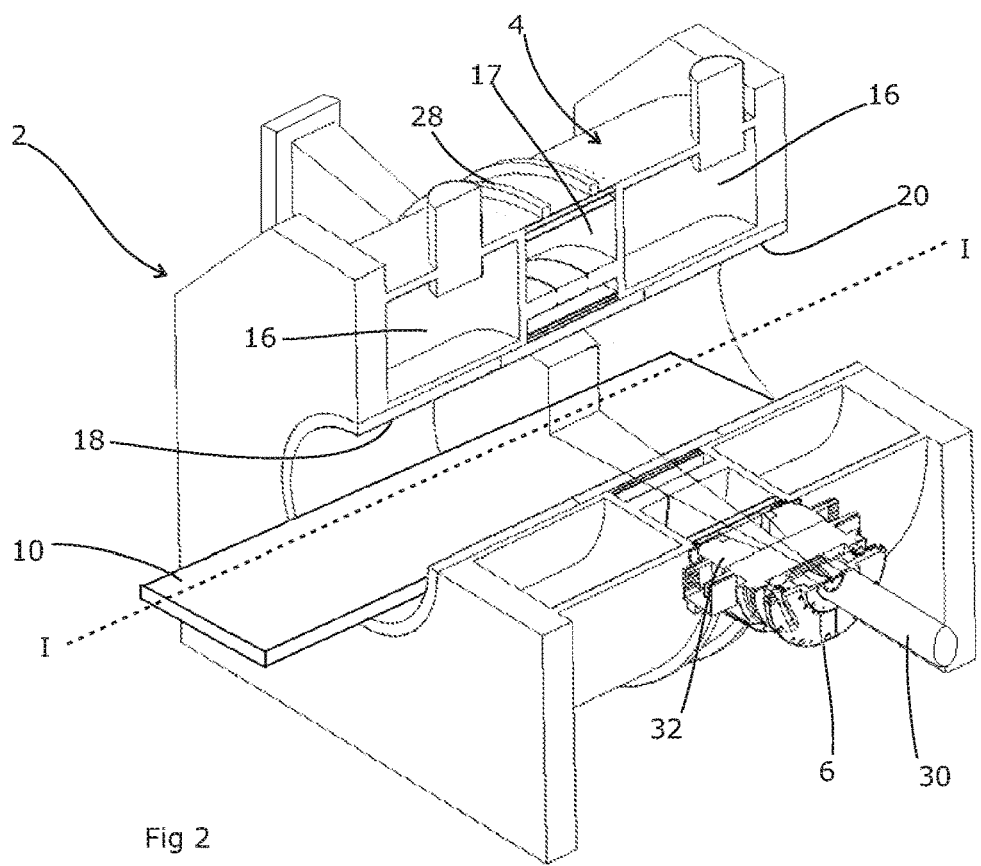

CONTROL OF BREATHING DURING MRI-BASED PROCEDURES

CROSS-REFERENCE TO RELATED PATENT APPLICATIONS

This application is a national phase of International Application No. PCT/EP2015/062942, filed on Jun. 10, 2015, which claims priority to United Kingdom Patent Application No. 1411246.0, filed on Jun. 25, 2014. The contents of the above-referenced applications are expressly incorporated herein by reference in their entireties.

FIELD OF THE INVENTION

The present invention relates to the control of breathing during medical procedures that include an MRI-based component.

BACKGROUND ART

MRI scanning processes are sensitive to movement of the patient's anatomy that is being scanned. It takes time to acquire a complete k-space data set (the Fourier data set from which an MRI image is computed), typically a minute or so, and any movement will result in different parts of the sampled k-space data set being obtained with the patient's anatomy in different positions. This inconsistency in the data set will create motion artefacts in the final image. The motion of the anatomy may be due to the respiratory and cardiac cycles of the patient.

A similar problem arises during radiotherapy; respiration causes tumours or other lesions in the chest area to move in synchrony. This presents problems in targeting the radiation at the tumour, as the tumour's position at any one time is uncertain. To achieve the primary objective of radiotherapy which is to irradiate the tumour, a margin around the nominal tumour position is used to compensate for this uncertainty, meaning that additional healthy tissue is irradiated.

To limit MRI artefacts during scanning and to reduce the radiotherapy treatment margin, measures are taken to control the patient's breathing during a procedure. These include simply asking the patient to hold their breath, sometimes with the assistance of an audible or visual prompt, or the use of devices such as respiratory belts, skin-mounted markers and the like which offer proxy data relating to respiration. A further alternative is the "Active Breathing Control" device, or "ABC", which comprises a face mask or breathing tube through which the patient breathes and which includes a pneumotachograph for measuring air flow rate. This rate information is integrated to produce lung filling information, and a valve in the flow path is closed to enforce a breath hold at a specific lung filling volume. The aim is to produce repeated static episodes in which the patient's anatomy is in a reproducible position, which can then be used for radiotherapy or for k-space data acquisition.

In MRI imaging, it is also possible to retrospectively select k-space data on the basis of respiratory-cycle information that was acquired during scanning. Most MRI apparatus allows for a fast acquisition of 1-dimensional line data or 2-dimensional slice data, the former being usually known as the "navigator channel". This can be used to identify features within the anatomy such as the diaphragm, from which the breathing phase can be determined. By selecting k-space data taken at like points in the breathing phase, an image without respiratory artefacts can be created.

U.S. Pat. No. 7,393,329 (Wong et al) suggests using an ABC device during radiotherapy, gating delivery of radiotherapy to periods of enforced breath hold. Wong et al (incorporated herein by reference) provides a good explanation of the operation of an ABC, and the reader is directed to Wong et al for a fuller understanding of the present invention.

Arnold et al ("*Lung MRI Using an MR-Compatible Active Breathing Control (MR-ABC)*"), Magnetic Resonance in Medicine 58:1092-1098 (2007) suggest combining an ABC device with an ECG to monitor cardiac activity during MRI scanning. Using an enforced breath hold of 1.5 seconds means that at least one cardiac cycle will take place during the breath hold, allowing k-space acquisition to be triggered by the cardiac R-wave to capture an image of a completely stationary anatomy. It also teaches triggering the valve to close when a flow reversal is detected rather that at a specific lung filling volume. This causes a breath hold at maximum exhalation, which is said to be a more reproducible point. The MR data acquisition is triggered indirectly; the valve trigger is fed to the ECG, which then produces a pulse after the next cardiac R-wave, and the pulse initiates the data acquisition.

SUMMARY OF THE INVENTION

The present invention is based on the realisation that the valve of the ABC device can be driven by an output derived from the navigator channel (or another fast-acquisition output) of the MRI scanner, rather than by inference from the measured flow rate. This has the advantage that the MRI output can yield a first-hand measurement of the diaphragm position or the tumour position. The computed lung volume obtained from a pneumotachograph is subject to drift over time for a variety of reasons, so a direct measurement of the anatomy will be more reliable. Where the MRI scanner is integrated with a radiotherapy device, the MRI data can be used to trigger the enforced breath-hold by the ABC, and the radiotherapy delivered while the ABC valve is shut. If the MRI data pertains to the actual position of the tumour, then the ABC device will (in effect) hold the tumour at a precise and reproducible point for treatment.

The present invention therefore provides an apparatus for imaging a patient, comprising a magnetic-resonance imager, a breath control device comprising a selectively-closeable valve adapted to prevent breath flow in at least one direction, and a control apparatus adapted to obtain a scan of the patient with the magnetic-resonance imager to yield an output image with fewer than three dimensions, analyse the output image, and if the output meets a defined criterion, close the valve to prevent breathing. The control apparatus may be adapted to determine from the output image the position of a diaphragm or a tumour of the patient, as noted in the previous paragraph.

In this way, a fast one- or two-dimensional scan (preferably one-dimensional) is performed which reveals enough about the patient anatomy to determine the breathing phase. Thus, a one-dimensional navigator scan can be performed along a line that includes (say) the diaphragm or the tumour. Previous three-dimensional scans may have revealed the range of movement of each; there may be motion artefacts in such scans but these will in fact give an indication of the range of movement. The navigator channel can then be aligned relative to the patient based on the result of these scans.

This functionality can be used to improve either MRI scanning techniques, or radiotherapy techniques. Generally, the non-ionising nature of MRI scanning means that there is no especial benefit in reducing the number of scans performed. Therefore, it will often be easier to scan the patient continuously (without an ABC) and retrospectively select k-space data which the navigator channel indicates were timed to share a common breathing phase. However, where the MRI scan is a preliminary step prior to radiotherapy, such as the acquisition of image data for treatment planning, it will be advantageous to obtain an image of the anatomy in the position in which it will be treated.

Thus, where the technique is used to improve MRI scanning, the control apparatus is preferably further adapted to trigger a scan of the patient to yield a three-dimensional output while the valve is closed. Eventually, the valve will open, in response to either a timer or to an override by the patient. At this point, the control apparatus is preferably adapted to suspend the triggered scan. It can then continue to scan the patient with the magnetic-resonance imager to yield an output image with fewer than three dimensions, analyse that output image, and when the output once again meets the defined criterion, close the valve to prevent breathing and resume the suspended scan. Thus, the full three-dimensional scan may be derived from k-space data acquired over one or more breath holds.

When used to improve radiotherapy, the imaging apparatus defined above can be integrated with a source of radiation adapted to deliver therapeutic radiation, and the control apparatus can be further adapted to trigger delivery of radiation by the source of radiation while the valve is closed. In this way, radiation is delivered while the tumour is in a known and reproducible position. There may or may not also be a three-dimensional MRI scan over the same period.

The breath control device can comprise a face mask attachable to a patient, or the like. Other forms include a tube through which the patient can breathe, often combined with a nasal clip to prevent leakage.

BRIEF DESCRIPTION OF THE DRAWINGS

An embodiment of the present invention will now be described by way of example, with reference to the accompanying figures in which;

FIG. 1 shows a partial view of a patient in the process of scanning and treatment;
FIG. 2 shows the scanning and treatment apparatus.

DETAILED DESCRIPTION OF THE EMBODIMENTS

Figure 3:
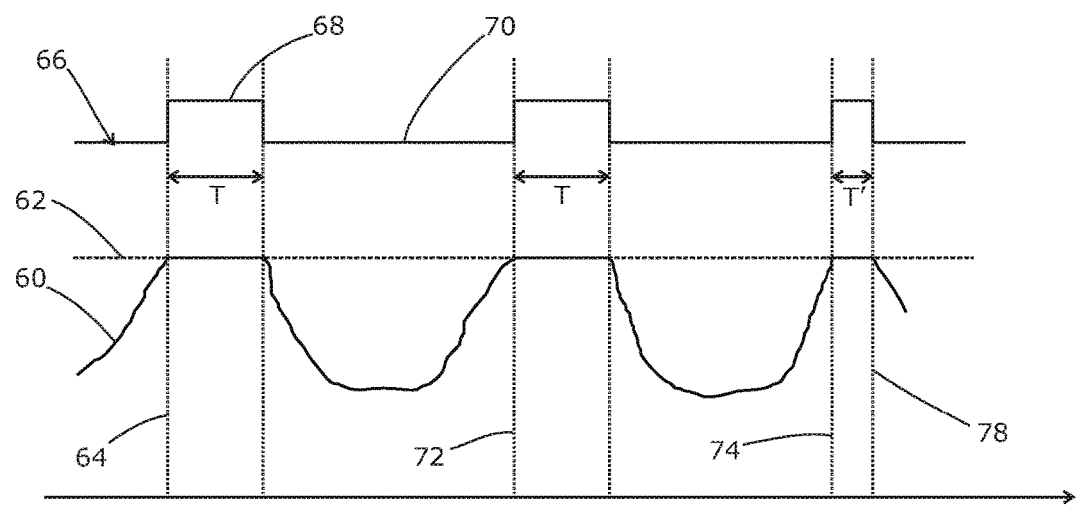
FIG. 3 shows a timing diagram for the apparatus.

FIGS. 1 and 2 show a system 2 according to embodiments of the present invention, comprising a radiotherapy apparatus 6 and a magnetic resonance imaging (MRI) apparatus 4. A patient 5 is present in FIG. 1 and shown in part, but is not present in FIG. 2.

The system includes a couch 10, for supporting the patient 5 in the apparatus. The couch 10 is movable along a horizontal, translation axis (labelled "I"), such that a patient resting on the couch is moved into the radiotherapy and MRI apparatus. In one embodiment, the couch 10 is rotatable around a central vertical axis of rotation, transverse to the translation axis, although this is not illustrated. The couch 10 may form a cantilever section that projects away from a support structure (not illustrated). In one embodiment, the couch 10 is moved along the translation axis relative to the support structure in order to form the cantilever section, i.e. the cantilever section increases in length as the couch is moved and the lift remains stationary. In another embodiment, both the support structure and the couch 10 move along the translation axis, such that the cantilever section remains substantially constant in length, as described in our earlier patent application published as WO 2009/007737, the contents of which are incorporated by reference and to which the skilled person is referred for a full understanding of the described embodiment.

As mentioned above, the system 2 also comprises an MRI apparatus 4, for producing near real-time imaging of a patient positioned on the couch 10. The MRI apparatus includes a primary magnet 16 which acts to generate the so-called "primary" magnetic field for magnetic resonance imaging. That is, the magnetic field lines generated by operation of the magnet 16 run substantially parallel to the central translation axis I. The primary magnet 16 consists of one or more coils with an axis that runs parallel to the translation axis I. The one or more coils may be a single coil or a plurality of coaxial coils of different diameter. In one embodiment (illustrated), the one or more coils in the primary magnet 16 are spaced such that a central window 17 of the magnet 16 is free of coils. In other embodiments, the coils in the magnet 16 may simply be thin enough or of a reduced density such that they are substantially transparent to radiation of the wavelength generated by the radiotherapy apparatus. The magnet 16 may further comprise one or more active shielding coils, which generates a magnetic field outside the magnet 16 of approximately equal magnitude and opposite polarity to the external primary magnetic field. The more sensitive parts of the system 2, such as the accelerator 30, are positioned in this region outside the magnet 16 where the magnetic field is cancelled, at least to a first order.

The MRI apparatus 4 further comprises two gradient coils 18, 20, which generate the so-called "gradient" magnetic field that is superposed on the primary magnetic field. These coils 18, 20 generate a gradient in the resultant magnetic field that allows spatial encoding of the protons so that their position can be determined, for example the gradient coils 18, 20 can be controlled such that the imaging data obtained has a particular orientation. The gradient coils 18, 20 are positioned around a common central axis with the primary magnet 16, and are displaced from one another along that central axis. This displacement creates a gap, or window, between the two coils 18, 20. In an embodiment where the primary magnet 16 also comprises a central window between coils, the two windows are aligned with one another.

An RF system causes the protons to alter their alignment relative to the magnetic field. When the RF electromagnetic field is turned off the protons return to the original magnetization alignment. These alignment changes create a signal which can be detected by scanning. The RF system may include a single coil that both transmits the radio signals and receives the reflected signals, dedicated transmitting and receiving coils, or multi-element phased array coils, for example. Control circuitry (not shown) controls the operation of the various coils 16, 18, 20 and the RF system, and signal-processing circuitry receives the output of the RF system, generating therefrom images of the patient supported by the couch 10.

As mentioned above, the system 2 further comprises a radiotherapy apparatus 6 which delivers doses of radiation to a patient supported by the couch 10. The majority of the radiotherapy apparatus 6, including at least a source of radiation 30 (e.g. an x-ray source and a linear accelerator) and a multi-leaf collimator (MLC) 32, is mounted on a chassis 28. The chassis 28 is continuously rotatable around the couch 10 when it is inserted into the treatment area, powered by one or more chassis motors. A radiation detector may also be mounted on the chassis 28 if desired, ideally opposite the radiation source 30 and with the rotational axis of the chassis positioned between them. The radiotherapy apparatus 6 further comprises control circuitry, which may be integrated within the system 2 shown in FIG. 1 or remote from it, and controls the radiation source 30, the MLC 32 and the chassis motor.

The radiation source 30 is positioned to emit a beam of radiation through the window defined by the two gradient coils 18, 20, and also through the window 17 defined in the primary magnet 16. The radiation beam may be a cone beam or a fan beam, for example.

In other embodiments, the radiotherapy apparatus 6 may comprise more than one source and more than one respective multi-leaf collimator.

In operation, a patient is placed on the couch 10 and the couch is inserted into the treatment area defined by the magnetic coils 16, 18 and the chassis 28. Control circuitry controls the radiation source 30, the MLC 32 and the chassis motor to deliver radiation to the patient through the window between the coils 16, 18. The chassis motor is controlled such that the chassis 28 rotates about the patient, meaning the radiation can be delivered from different directions. The MLC 32 has a plurality of elongate leaves oriented orthogonal to the beam axis; an example is illustrated and described in our EP-A-0,314,214, the content of which is hereby incorporated by reference and to which the reader is directed in order to obtain a full understanding of the described embodiment. The leaves of the MLC 32 are controlled to take different positions blocking or allowing through some or all of the radiation beam, thereby altering the shape of the beam as it will reach the patient. Simultaneously with rotation of the chassis 28 about the patient, the couch 10 may be moved along a translation axis into or out of the treatment area (i.e. parallel to the axis of rotation of the chassis). With this simultaneous motion a helical radiation delivery pattern is achieved, known to produce high quality dose distributions.

The patient 5, reclining on the couch 10, is provided with a breath control device 50. This comprises a breathing tube 52 which the patient places in their mouth. A nasal clip 54 ensures that all breathing by the patient must be through the breathing tube 52, which is connected to a hose 56 through which fresh air, oxygen, or a breathable mix is supplied. Alternatively, the breathing tube 54 may open to the atmosphere. The breathing tube 54 includes a selectively-operable valve 58 which can close or open the breathing tube 54 to passage of air at will. This is ideally controlled via a cable extending alongside and carried by the hose 56.

FIG. 3 shows a possible timing diagram for use in this invention. As time passes from left to right, a position 60 of a relevant feature in the navigator channel is tracked. When this rises to reach a threshold level 62 (at time point 64), a signal 66 to the valve 58 is changed to a "closed" state 68. As the position of the feature is dictated by the lung filling, closing the valve forces a breath hold by the patient which immobilises the relevant feature and other features that are also dictated by lung filling. Thus, where the relevant feature is (for example) the diaphragm position, other positionally-associated features such as a lung tumour or a breast tumour are also immobilised. Where the relevant feature is the tumour itself, it will naturally be immobilised at the threshold position. The signal 66 can also be fed to the MRI scanner or the radiotherapy apparatus, as relevant, as a "permit" signal to allow further treatment.

After a predetermined period of time T, the signal 66 drops to an "open" state 70. This transition in the signal prompts the scanning or treatment to cease and the valve 58 to open, allowing the patient to breathe again. A time period of up to about 15 seconds should be adequate to allow sufficient treatment or scanning time, but without causing discomfort to the patient. If desired, a separate signal to the MRI scanner or radiotherapy treatment apparatus could be employed, dropping to the open state 70 at T-ε, i.e. slightly before the valve opens in order to allow a safety margin.

The patient then breathes out, and on the next 'in' breath the relevant feature moves back towards the threshold 62 at time 72. The process then repeats.

As a safety feature, a "panic" button can be provided for the patient to force the signal 66 to drop to an open state if they wish or need to breathe out. This is shown at time 78, where the signal 66 drops after a shorter time T' when the patient activates the panic button. MRI scanning and/or radiotherapy treatment then cease immediately.

Figure 4:
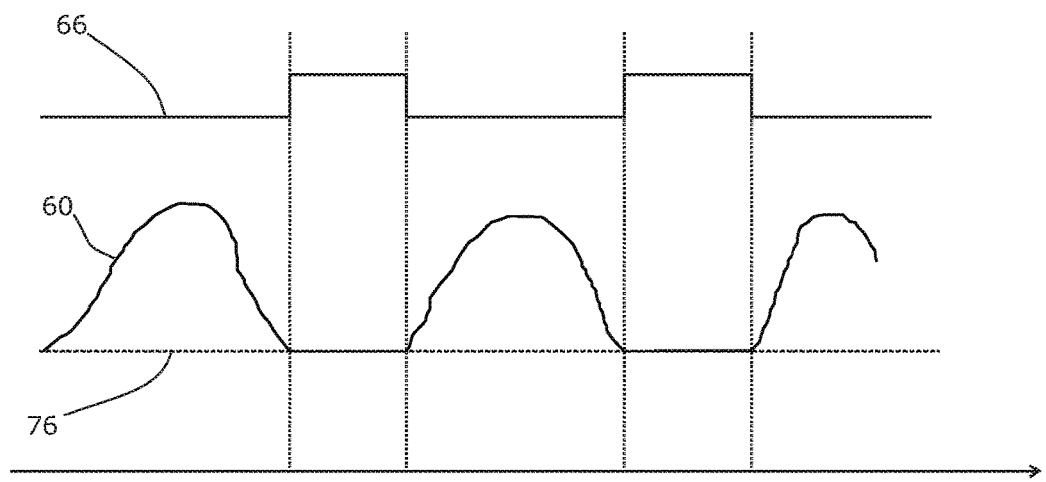
FIG. 4 shows an alternative timing diagram.

FIG. 4 shows an alternative arrangement in which a low threshold 76 is used instead. Thus, when the reported position 60 of the relevant feature drops to that threshold, the signal 66 is activated to close the valve 58. This might allow the patient to hold their breath on an exhale, or may cater for the use of relevant features whose position is anti-correlated with lung filling.

Thus, the present invention allows a more accurate and reliable trigger for active breathing control devices, which relay on real-time information from the patient anatomy instead of proxy information that may be subject to inaccuracies and/or drift. It will of course be understood that many variations may be made to the above-described embodiment without departing from the scope of the present invention.

The invention claimed is:
1. An apparatus for imaging a patient, comprising:
a magnetic-resonance imager;
a breath control device comprising a selectively-closeable valve adapted to prevent breath flow in at least one direction; and
a control apparatus configured to:
obtain a first scan of the patient with the magnetic-resonance imager (MRI) to yield a first MRI output image with fewer than three dimensions;
analyze the first MRI output image to determine if the first MRI output image meets a first defined criterion associated with whether the patient is in a breathing phase;
if the first MRI output image meets the first defined criterion, close the valve to prevent breathing for a first predetermined period of time;
trigger a second scan of the patient to yield a second MRI output image while the valve is closed during the first predetermined period of time, wherein the second MRI output image is three-dimensional; and
enable the second scan to resume during a subsequent closing of the valve for a second predetermined period of time.

2. The apparatus according to claim 1, wherein the control apparatus is configured to determine from the first MRI output image the position of a diaphragm or a tumor of the patient.

3. The apparatus according to claim 1, wherein the first scan is a one-dimensional scan.

4. The apparatus according to claim 1, wherein the breath control device comprises a face mask attachable to the patient.

5. The apparatus according to claim 1, wherein the control apparatus is configured to, after the first predetermined period of time ends, suspend the second scan when the valve subsequently opens.

6. The apparatus according to claim 5, wherein the valve subsequently opens based on a patient override prior to an end of the first predetermined period of time.

7. The apparatus according to claim 5, wherein the control apparatus is configured to, after the valve subsequently opens:
obtain a third scan of the patient with the MRI to yield a third MRI output image with fewer than three dimensions;
analyze the third MRI output image; and
close the valve to prevent breathing for the second predetermined period of time while the third MRI output image meets a second defined criterion.

8. An apparatus for radiotherapy, comprising:
a magnetic-resonance imager;
a breath control device comprising a selectively-closeable valve adapted to prevent breath flow in at least one direction;
a source of radiation adapted to deliver therapeutic radiation; and
a control apparatus configured to:
obtain a first scan of a patient with the magnetic-resonance imager (MRI) to yield a first (MRI) output image;
determine whether to close the valve based on the first MRI output image;
trigger, while the valve is closed for a first predetermined period of time, delivery of radiation by the source of radiation and a second scan of the patient to yield a second MRI output image, wherein the second output image is three-dimensional; and
enable the second scan to resume during a subsequent closing of the valve for a second predetermined period of time.

9. The apparatus according to claim 8, wherein the breath control device comprises a face mask attachable to the patient.

10. The apparatus according to claim 8, wherein the control apparatus is configured to determine from the first MRI output image the position of a diaphragm or a tumor of the patient.

11. The apparatus according to claim 8, wherein the first scan is a one-dimensional scan.

12. The apparatus according to claim 8, wherein the control apparatus is configured to, after the first predetermined period of time ends, suspend the second scan when the valve subsequently opens.

13. The apparatus according to claim 12, wherein the control apparatus is configured to, after the valve subsequently opens:
obtain a third scan of the patient with the MRI to yield a third MRI output image with fewer than three dimensions;
analyze the third MRI output image; and
close the valve to prevent breathing for the second predetermined period of time while the third MRI output image meets a second defined criterion.

14. A method of controlling an imaging apparatus for imaging a patient, comprising:
obtaining a first scan of a patient with a magnetic-resonance imager to yield a first MRI output image with fewer than three dimensions;
analyzing the first MRI output image to determine if the first MRI output image meets a first defined criterion associated with whether the patient is in a breathing phase;
closing, for a first predetermined period of time, a selectively-closeable valve configured to prevent breath flow in at least one direction if the first MRI output image meets a first defined criterion;
triggering a second scan of the patient to yield a second MRI output image while the valve is closed during the first predetermined period of time, wherein the second MRI output image is three-dimensional; and
enabling the second scan to resume during a subsequent closing of the valve for a second predetermined period of time.

15. The method according to claim 14, further comprising determining from the first MRI output image the position of a diaphragm or a tumor of the patient.

16. The method according to claim 14, wherein the first scan is a one-dimensional scan.

17. The method according to claim 14, further comprising delivering radiation to the patient from a source of radiation when the valve is closed.

18. The method according to claim 14, further comprising, after the first predetermined period of time ends, suspending the second scan when the valve subsequently opens.

19. The method according to claim 18, further comprising, after the valve subsequently opens:
obtaining a third scan of the patient with the MRI to yield a third MRI output image with fewer than three dimensions;
analyzing the third MRI output image; and
closing the valve to prevent breathing for the second predetermined period of time while the third MRI output image meets a second defined criterion.

20. An apparatus for imaging a patient, comprising:
a magnetic-resonance imager;
a breath control device comprising a selectively-closeable valve adapted to prevent breath flow in at least one direction; and
a control apparatus configured to:
obtain a first scan of the patient with the magnetic-resonance imager (MRI) to yield a first output image with fewer than three dimensions;
analyze the first output image to determine if the first output image meets a first defined criterion associated with whether the patient is in a breathing phase;
if the first output image meets the first defined criterion, close the valve to prevent breathing for a first predetermined period of time and trigger a second scan of the patient with the MRI to yield a second output image; and
resume the second scan during a subsequent closing of the valve for a second predetermined period of time.

* * * * *